US009956240B2

(12) United States Patent
D'Antonio et al.

(10) Patent No.: US 9,956,240 B2
(45) Date of Patent: May 1, 2018

(54) THERAPEUTIC MONOSACCHARIDE-BASED INHIBITORS OF HEXOKINASE AND GLUCOKINASE FOR PARASITIC DISEASES, ALONG WITH METHODS OF THEIR FORMATION AND USE

(71) Applicant: University of South Carolina, Columbia, SC (US)

(72) Inventors: Edward L. D'Antonio, Bluffton, SC (US); Jennifer D'Antonio, Bluffton, SC (US)

(73) Assignee: University of South Carolina, Columbia, SC (US)

( * ) Notice: Subject to any disclaimer, the term of this patent is extended or adjusted under 35 U.S.C. 154(b) by 66 days.

(21) Appl. No.: 14/880,098

(22) Filed: Oct. 9, 2015

(65) Prior Publication Data
US 2016/0145291 A1 May 26, 2016

Related U.S. Application Data

(60) Provisional application No. 62/082,861, filed on Nov. 21, 2014, provisional application No. 62/175,485, filed on Jun. 15, 2015.

(51) Int. Cl.
| | | |
|---|---|---|
| A61K 31/7008 | (2006.01) | |
| C07H 5/06 | (2006.01) | |
| C07H 13/04 | (2006.01) | |
| C07H 13/08 | (2006.01) | |
| C07H 13/12 | (2006.01) | |

(52) U.S. Cl.
CPC .......... *A61K 31/7008* (2013.01); *C07H 5/06* (2013.01); *C07H 13/04* (2013.01); *C07H 13/08* (2013.01); *C07H 13/12* (2013.01)

(58) Field of Classification Search
None
See application file for complete search history.

(56) References Cited

U.S. PATENT DOCUMENTS 6,723,710 B2   4/2004  Christianson et al.

FOREIGN PATENT DOCUMENTS

| WO | WO 0035944 | 6/2000 | |
| WO | WO 0035944 A1 * | 6/2000 | ............. C07H 17/02 |

OTHER PUBLICATIONS

Doerig, C. (2004). Protein kinases as targets for anti-parasitic chemotherapy. Biochimica et Biophysica Acta (BBA)-Proteins and Proteomics, 1697(1), 155-168.*
Heussler, V. T., Rottenberg, S., Schwab, R., Küenzi, P., Fernandez, P. C., McKellar, S., . . . & Dobbelaere, D. A. (2002). Hijacking of host cell IKK signalosomes by the transforming parasite Theileria. Science, 298(5595), 1033-1036.*
d'Abusco, A. S., Politi, L., Giordano, C., & Scandurra, R. (2010). A peptidyl-glucosamine derivative affects IKKa kinase activity in human chondrocytes.*
Willson, M., Sanejouand, Y. H., Perie, J., Hannaert, V., & Opperdoes, F. (2002). Sequencing, modeling, and selective inhibition of Trypanosoma brucei hexokinase. Chemistry & biology, 9(7), 839-847. (Year: 2002).*
D'Abusco, et al. "A peptidyl-glucosamine derivative affects IKKα kinase activity in human chondrocytes."
Doerig, C. (2004) Protein kinases as targets for anti-parasitic chemotherapy. Biochimica et Biophysica Acta (BBA)—Proteins and Proteomics, 1697 (1), 155-168.
Heussler, V., et al. (2002). "Hijacking of Host Cell IDD Signalosomes by the Transforming Parasite Theileria," Science, 298 (5595) 1033-1036.
Lefebvre et al., "Mononucleoside Phosphotriester Derivatives with S-Acyl-2-thioethyl Bioreversible Phosphate-Protecting Groups: Intracellular Delivery of 3'-Azido-2',3'-dideoxythymidine 5'-Monophosphate," J. Med. Chem. 1995, 38, 3941-3950.
Ling, et al. "A method for fast shot boundary detection based on SVM," IEEE Image and Signal Process (2008).
Ruda et al., "Aryl Phosphoramidates of 5-Phospho Erythronohydoxamic Acid, a New Class of Potent Trypanocidal Compounds," J. Med. Chem. 2010, 53, 6071-6078.
Ruda et al., "Synthesis and Biological Evaluation of Phosphate Prodrugs of 4-Phospho-D-erythronohydoxamic Acid, an Inhibitor of 6-Phosphogluconate Dehydrogenase," ChemMedCbem, 2007, 2, 1169-1180.
Wilson et al., "Sequencing, Modeling and Selective Inhibition of Trypanosoma brucei Hexokinase," Chemistry & Bilogy, vol. 9, 839-847 Jul. 2002.

* cited by examiner

*Primary Examiner* — James H Alstrum-Acevedo
*Assistant Examiner* — Dale R Miller
(74) *Attorney, Agent, or Firm* — Dority & Manning, PA

(57) ABSTRACT

Methods for treating a mammal that is infected by a parasitic organism are provided, along with pharmaceutical compositions and compounds. The method includes administering to the mammal the pharmaceutical composition of FIG. 1, where: $R_1$, $R_2$, $R_3$, and $R_4$ comprises, independently, H, OH, $NH_2$, SH, a halogen, or an organic group or a derivative thereof; $X_1$ is O, NH, $CH_2$, or S; m is 0 or 1; $X_2$ comprises an organic linkage, such as $CH_2$; n is an integer from 0 to 10; and $R_5$ comprises an aromatic organic group.

15 Claims, 6 Drawing Sheets

THERAPEUTIC MONOSACCHARIDE-BASED INHIBITORS OF HEXOKINASE AND GLUCOKINASE FOR PARASITIC DISEASES, ALONG WITH METHODS OF THEIR FORMATION AND USE

PRIORITY INFORMATION

The present application claims priority to U.S. Provisional Patent Application Ser. No. 62/082,861 titled "Therapeutic Monosaccharide-based Inhibitors of Hexokinase and Glucokinase for Parasitic Diseases, along with Methods of Their Formation and Use" of D'Antonio, et al. filed on Nov. 21, 2014 and to U.S. Provisional Patent Application Ser. No. 62/175,485 titled "Therapeutic Monosaccharide-based Inhibitors of Hexokinase and Glucokinase for Parasitic Diseases, along with Methods of Their Formation and Use" of D'Antonio, et al. filed on Jun. 15, 2015; the disclosures of which are incorporated by reference herein.

FIELD OF THE TECHNOLOGY

This invention relates generally to enzyme inhibitors, more particularly to inhibitors of the enzymes hexokinase and glucokinase.

BACKGROUND

Trypanosomal parasites, such as *Trypanosoma cruzi* (*T. cruzi*) and *Trypanosoma brucei* (*T. brucei*), utilize glycolysis which is an essential energy-producing metabolic pathway. Since glycolysis is indispensable for these organisms, obstruction of the pathway leads to cell death and can be caused by inhibition (using a drug) of two similar enzymes, hexokinase and glucokinase. In order to create a therapeutic drug, an inhibitor would need to selectively block the parasite homologue and avoid cross-reactivity with the human homologue (bind weaker or not bind at all), giving rise to a good selectively ratio.

Chagas' disease has two standard-of-care treatments available, such as benznidazole and nifurtimox, which were developed over 35 years ago. African sleeping sickness has been reliant on a variety of drugs, such as pentamidine, suramin, eflornithine, and melarsoprol; however, all of these medicines (for both diseases) require substantial improvements in their tolerability, safety, and efficacy. Additionally, many of the currently available drugs for treatment are ineffective due to low cellular penetration with the drugs bearing phosphate or phosphonate groups.

As such, a need exists for new inhibitors of the enzymes hexokinase and glucokinase.

SUMMARY

Objects and advantages of the invention will be set forth in part in the following description, or may be obvious from the description, or may be learned through practice of the invention.

Methods are generally provided for treating a mammal that is infected by a parasitic organism. In one embodiment, the method includes administering to the mammal the pharmaceutical composition of FIG. 1, where: $R_1$, $R_2$, $R_3$, and $R_4$ comprises, independently, H, OH, $NH_2$, SH, a halogen, or an organic group or a derivative thereof; $X_1$ is O, NH, $CH_2$, or S; m is 0 or 1; $X_2$ comprises an organic linkage, such as $CH_2$; n is an integer from 0 to 10; and $R_5$ comprises an aromatic organic group.

Pharmaceutical compositions and compounds are also generally provided.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures, in which.

DEFINITIONS

Figure 1:
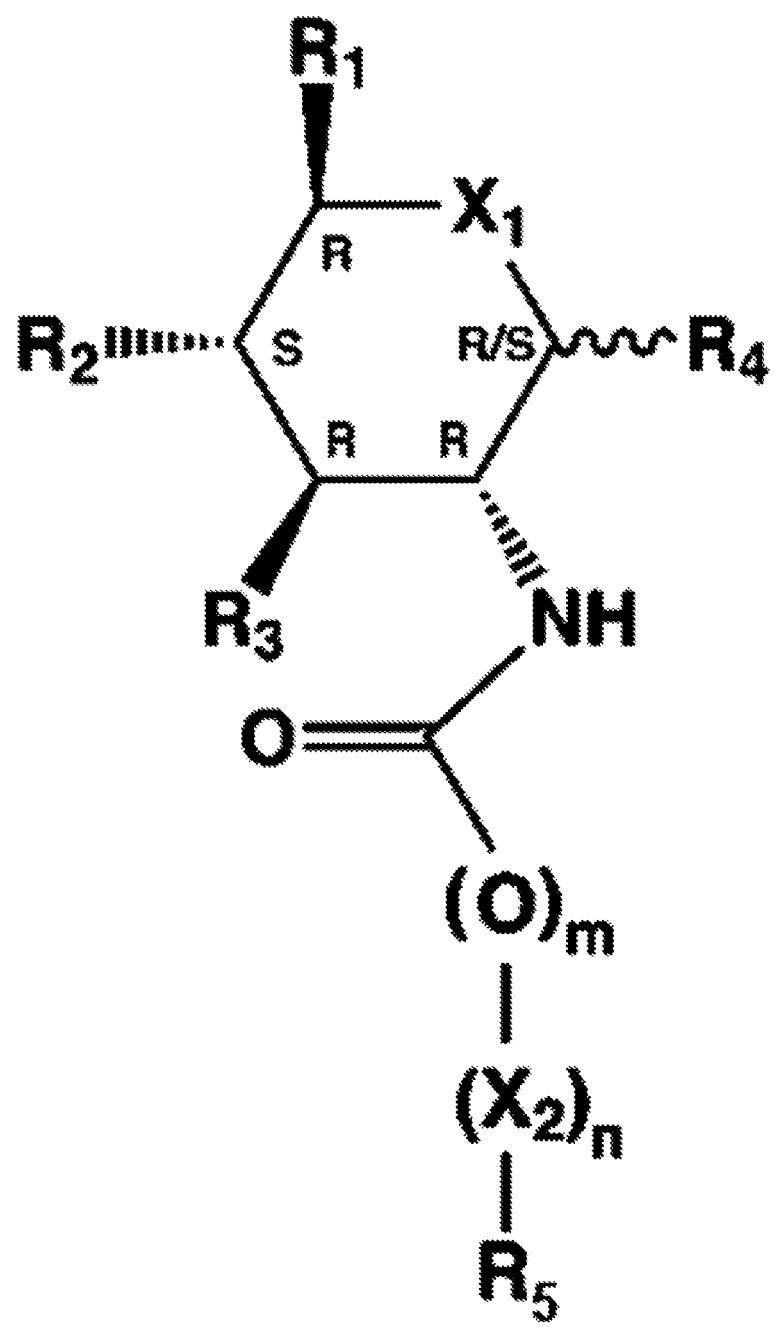
FIG. 1 shows an exemplary composition, including a glucokinase or hexokinase inhibitor.

Chemical elements are discussed in the present disclosure using their common chemical abbreviation, such as commonly found on a periodic table of elements. For example, hydrogen is represented by its common chemical abbreviation H; helium is represented by its common chemical abbreviation He; and so forth.

The term "organic" is used herein to refer to a class of chemical compounds that are comprised of carbon atoms. For example, an "organic polymer" is a polymer that includes carbon atoms in the polymer backbone, but may also include other atoms either in the polymer backbone and/or in side chains extending from the polymer backbone (e.g., oxygen, nitrogen, sulfur, etc.).

As used herein, the term "related compounds thereof" refers to compounds that have the basic structure of the base compound with substituted atom(s) and/or substituted side groups, while still keeping the functionality of the base compound.

The term "pharmaceutically effective amount" refers to the amount of a drug or pharmaceutical agent that will elicit the biological or medical response of a tissue, system, animal, or human that is being sought by a researcher or clinician. This amount can be a therapeutically effective amount.

The term "pharmaceutically acceptable carrier" is used herein to refer to a carrier that is useful in preparing a pharmaceutical composition that is generally safe, non-toxic and neither biologically nor otherwise-undesirable, and is acceptable for veterinary use as well as human pharmaceutical use. A "pharmaceutically acceptable carrier" as used in the specification and claims can include both one and more than one such carrier. By "pharmaceutically acceptable" it is meant the carrier must be compatible with the other ingredients of the formulation and not deleterious to the recipient thereof.

The terms "administration of" or "administering a" pharmaceutical composition should be understood to mean providing a pharmaceutical composition to an individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The term "treatment" or "treating" means any administration of a pharmaceutical composition to obtain a desired pharmacologic and/or physiologic effect. The effect may be prophylactic in terms of completely or partially preventing a disease or symptom thereof, and/or may be therapeutic in terms of a partial or complete cure for a disease and/or adverse affect attributable to the disease. Treatment includes (a) inhibiting the disease in the subject that is experiencing or displaying the pathology or symptomatology of the diseased (i.e., arresting further development of the pathology and/or symptomatology), or (b) ameliorating the disease in the subject that is experiencing or displaying the pathology or symptomatology of the diseased (i.e., reversing the pathology and/or symptomatology).

DETAILED DESCRIPTION

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

Compounds and methods are generally provided that can be used against certain validated drug-targets (i.e., glucokinase and hexokinase) that are found in protozoan parasites. The drugs proposed in this patent may serve as viable substitutes for the currently used drugs in the clinic, pending in-vitro parasite studies and mouse infectivity studies. The compounds described herein are experimentally-confirmed potent & selective inhibitors of *T. cruzi* glucokinase and hexokinase, as they were compared to *H. sapiens* glucokinase. The drug compounds described in this patent application may offer an alternative to the mainstream drugs that are used in the clinic for two diseases of the trypanosome, such as American Trypanosomiasis (Chagas' Disease) and Human African Trypanosomiasis (African Sleeping Sickness), caused by parasites *T. cruzi* and *T. brucei*, respectively.

I. Glucokinase and/or Hexokinase Inhibitor Compounds

In one embodiment, FIG. 1 shows an exemplary composition, including a glucokinase or hexokinase inhibitor, where:

$R_1$, $R_2$, $R_3$, and $R_4$ comprises, independently, H, OH, $NH_2$, SH, a halogen (e.g., F, Cl, Br, or I), or an organic group on the six-membered ring, such as an aliphatic hydrocarbon group (e.g., a methyl group, an ethyl group, etc.) or a derivative thereof (e.g., a hydroxymethyl group, etc.);

$X_1$ is O, NH, $CH_2$, or S;

m is 0 or 1;

$X_2$ comprises an organic linkage, such as $CH_2$;

n is an integer from 0 to 10 (e.g., 0, 1, 2, 3, 4, 5, or 6); and $R_5$ comprises an aromatic organic group, such as a benzene group, a benzene-derivative group (e.g., a phenol group, a toluene group, an aniline group, a heterocycle group such as pyridine, etc.), a polycyclic aromatic group (e.g., a naphthalene group, etc.) or their derivatives (e.g., a benzothiophene group, a benzofuran group, an indole group, an indazole group, a benzothiazole group, etc.). In particular embodiments of the composition, $R_2$ includes at least one oxygen moiety (e.g., a C=O group, an OH group, a sulfonyl group, etc.).

Figure 2A:
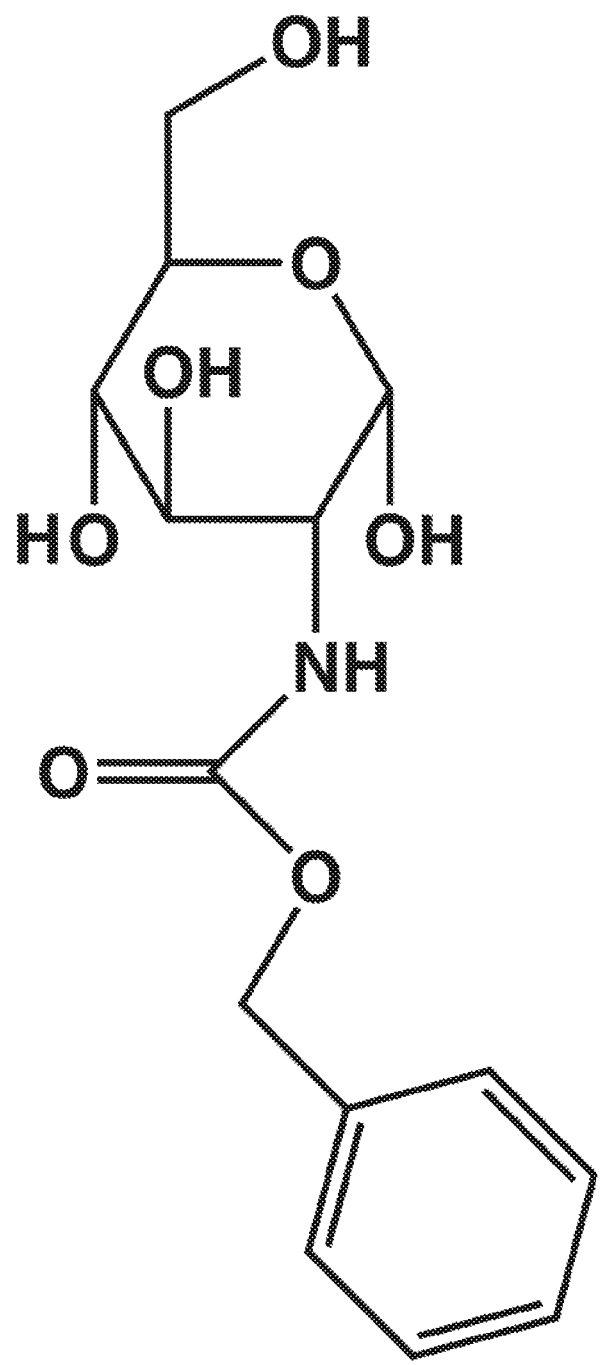
FIG. 2a shows an embodiment of the exemplary compound of FIG. 1, where $R_1$ is a hydroxymethyl group, $R_2$, $R_3$, and $R_4$ are each a hydroxyl group (—OH); $X_1$ is O; m is 1, $X_2$ is $CH_2$; n is 1; and $R_5$ is a benzene group.

FIG. 2a shows one embodiment of such a compound, where $R_1$ is a hydroxymethyl group, $R_2$, $R_3$, and $R_4$ are each a hydroxyl group (—OH); $X_1$ is O; m is 1, $X_2$ is $CH_2$; n is 1; and $R_5$ is a benzene group.

Figure 2B:
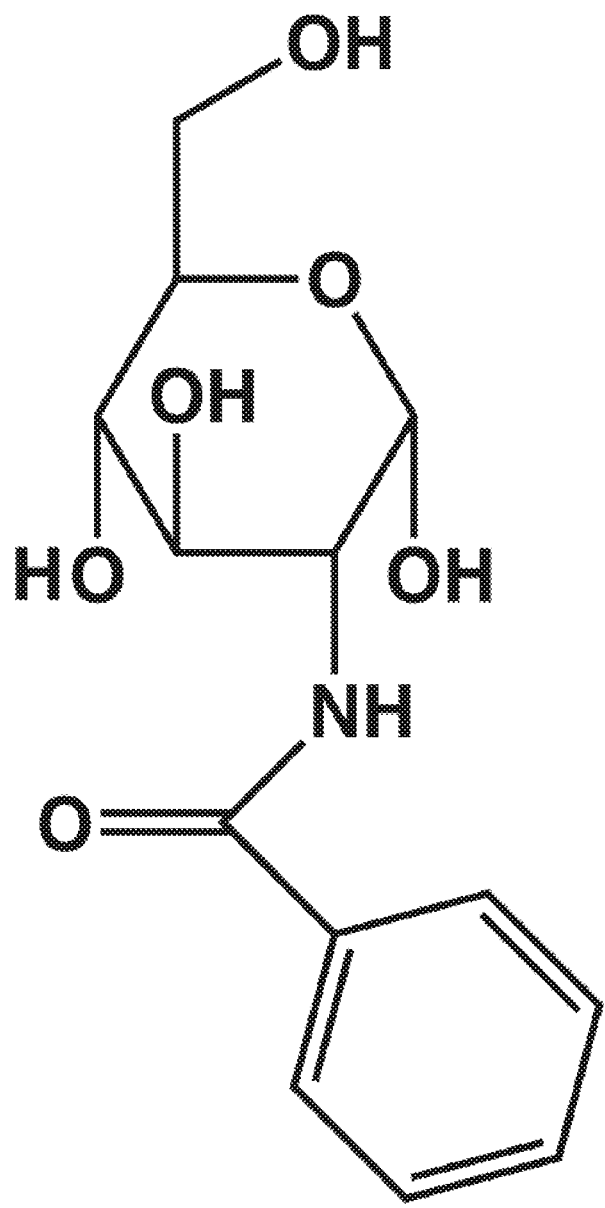
FIG. 2b shows another embodiment of the exemplary compound of FIG. 1, where $R_1$ is a hydroxymethyl group, $R_2$, $R_3$, and $R_4$ are each a hydroxyl group (—OH); $X_1$ is O; m is 0, n is 0; and $R_5$ is a benzene group.

FIG. 2b shows another embodiment of such a compound, where $R_1$ is a hydroxymethyl group, $R_2$, $R_3$, and $R_4$ are each a hydroxyl group (—OH); $X_1$ is O; m is 0, n is 0; and $R_5$ is a benzene group.

Figure 2C:
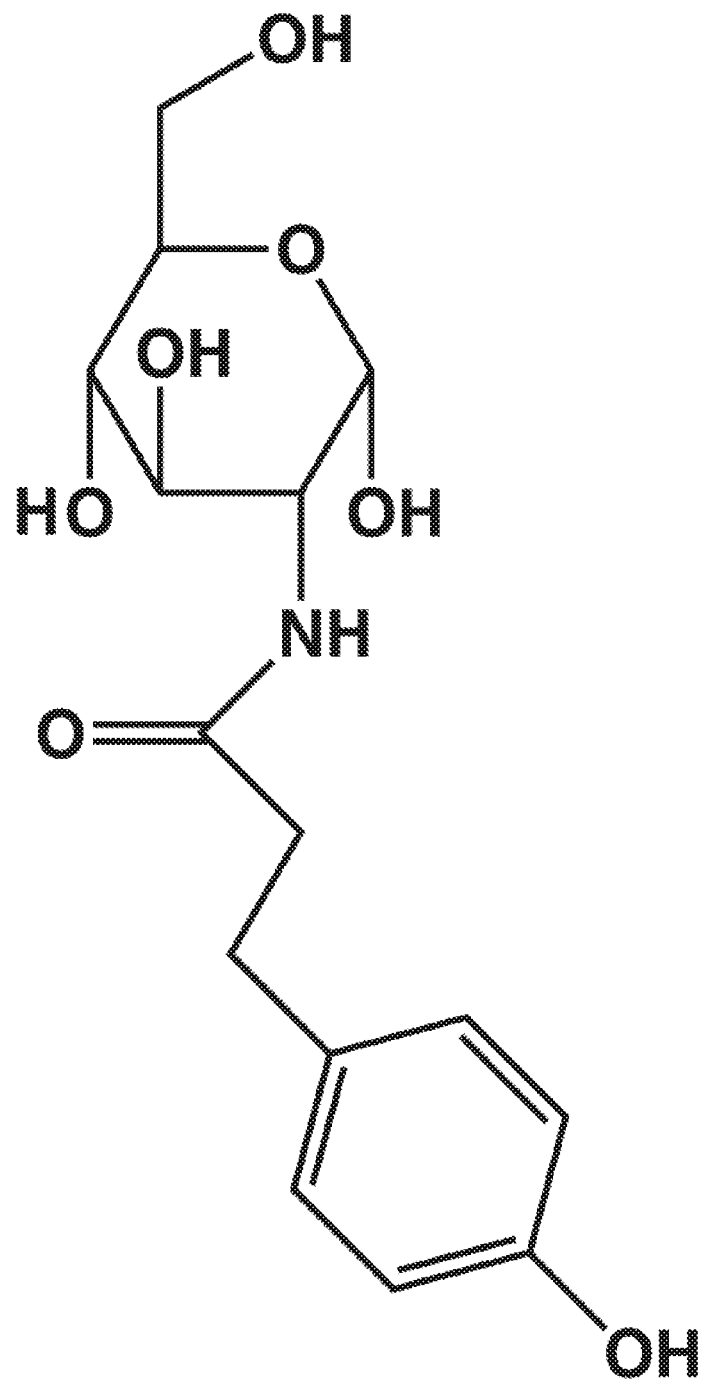
FIG. 2c shows yet another embodiment of the exemplary compound of FIG. 1, where $R_1$ is a hydroxymethyl group, $R_2$, $R_3$, and $R_4$ are each a hydroxyl group (—OH); $X_1$ is O; m is 0, $X_2$ is $CH_2$; n is 2; and $R_5$ is a phenol group

FIG. 2c shows yet another embodiment of such a compound, where $R_1$ is a hydroxymethyl group, $R_2$, $R_3$, and $R_4$ are each a hydroxyl group (—OH); $X_1$ is O; m is 0, $X_2$ is $CH_2$; n is 2; and $R_5$ is a phenol group.

Figure 2D:
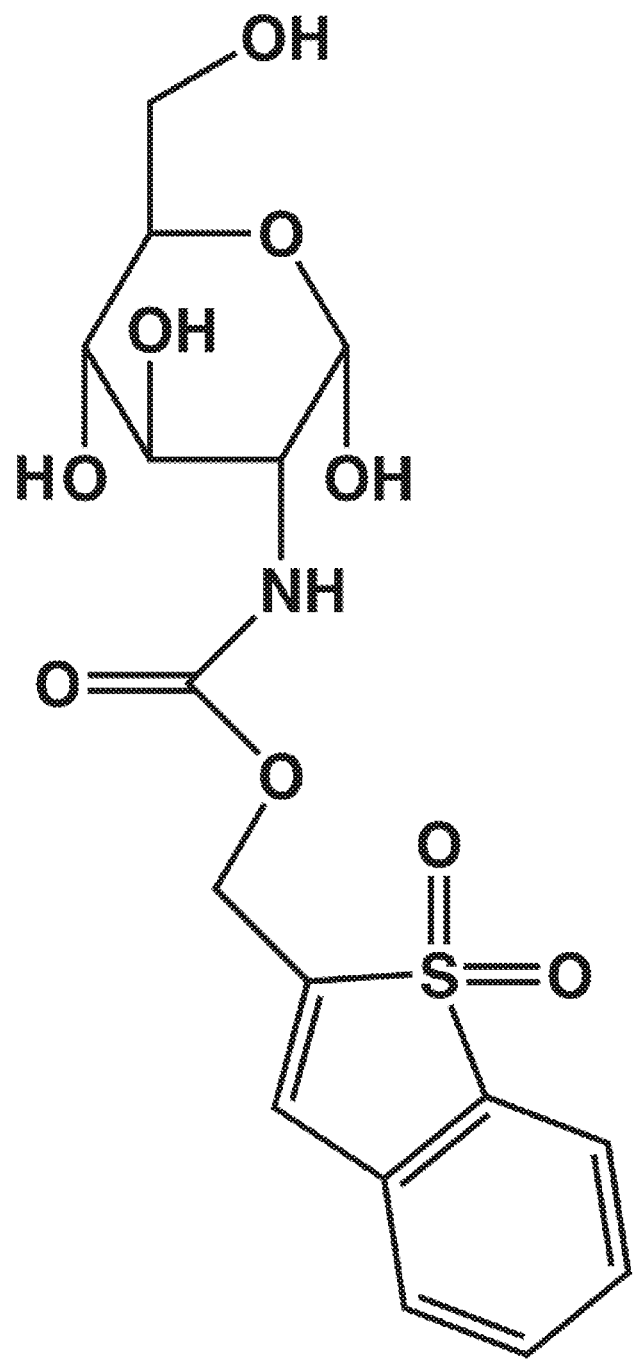
FIG. 2d shows still another embodiment of the exemplary compound of FIG. 1, where $R_1$ is a hydroxymethyl group, $R_2$, $R_3$, and $R_4$ are each a hydroxyl group (—OH); $X_1$ is O; m is 1, $X_2$ is $CH_2$; n is 1; and $R_5$ is a benzothiophene group with a sulfonyl group.

FIG. 2d shows still another embodiment of such a compound, where $R_1$ is a hydroxymethyl group, $R_2$, $R_3$, and $R_4$ are each a hydroxyl group (—OH); $X_1$ is O; m is 1, $X_2$ is $CH_2$; n is 1; and $R_5$ is a benzothiophene group with a sulfonyl group.

II. Pharmaceutical Compositions

In one embodiment, a pharmaceutical composition is generally provided that includes a pharmaceutically acceptable carrier and a glucokinase or hexokinase inhibitor having the structure as shown in FIG. 1, discussed above.

Pharmaceutical compositions may be prepared by any of the methods well known in the art of pharmacy. Pharmaceutical compositions encompass any compositions made by admixing the active ingredients and a pharmaceutically acceptable carrier. The carrier may take a wide variety of forms depending on the form of preparation desired for administration, e.g., oral or parenteral (including intravenous). Thus, the pharmaceutical composition can be presented as discrete units suitable for oral administration such as capsules, cachets, or tablets each containing a predetermined amount of the active ingredients. Further, the composition can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the composition may also be administered by controlled release means and/or delivery devices. The foregoing list is illustrative only and is not intended to be limiting in any way.

Pharmaceutical compositions intended for oral use may contain one or more agents selected from the group consisting of sweetening agents, flavoring agents, coloring agents and preserving agents in order to provide pharmaceutically elegant and palatable preparations. Tablets may contain a composition of FIG. 1 in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid, or talc. The tablets may be uncoated or they may be coated by known techniques to delay disintegration and absorption in the gastrointestinal tract and thereby provide a sustained action over a longer period. A tablet may be prepared by compression or molding, optionally with one or more accessory ingredients or adjuvants. Compressed tablets may be prepared by compressing, in a suitable machine, a compound of FIG. 1 in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent.

Pharmaceutical compositions for oral use may also be presented as hard gelatin capsules wherein the compound of FIG. 1 is mixed with an inert solid diluent, for example, calcium carbonate, calcium phosphate or kaolin, or as soft gelatin capsules wherein the compound of FIG. 1 is mixed with water or an oil medium, for example peanut oil, liquid paraffin, or olive oil.

Pharmaceutical compositions can also include aqueous suspensions, which contain the active materials in admixture with excipients suitable for the manufacture of aqueous suspensions. In addition, oily suspensions may be formulated by suspending the compound of FIG. 1 in a vegetable oil, for example arachis oil, olive oil, sesame oil or coconut oil, or in a mineral oil such as liquid paraffin. Oily suspensions may also contain various excipients. The pharmaceutical compositions of FIG. 1 may also be in the form of oil-in-water emulsions, which may also contain excipients such as sweetening and flavoring agents.

Pharmaceutical compositions can be in the form of a sterile injectable aqueous or oleaginous suspension, or in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage, and should be preserved against the contaminating action of microorganisms such as bacteria and fungi.

Pharmaceutical compositions can be in a form suitable for topical use such as, for example, an aerosol, cream, ointment, lotion, dusting powder, or the like. Further, the compositions can be in a form suitable for use in transdermal devices. These formulations may be prepared via conventional processing methods. As an example, a cream or ointment is prepared by mixing hydrophilic material and water, together with about 5 wt % to about 10 wt % of the compound of FIG. 1, to produce a cream or ointment having a desired consistency.

Pharmaceutical compositions can also be in a form suitable for rectal administration wherein the carrier is a solid. Suitable carriers include cocoa butter and other materials commonly used in the art.

III. Methods of Inhibiting Glucokinase or Hexokinase

Methods are also provided for inhibiting glucokinase or hexokinase, both in-vitro and in-vivo. In one embodiment, the method comprises contacting either the glucokinase or the hexokinase with a compound having the structure of FIG. 1, discussed above.

For instance, a method is provided for inhibiting glucokinase or hexokinase in a parasitic organism. This method comprises administering to the human a composition comprising a pharmaceutically acceptable carrier and a glucokinase or a hexokinase inhibitor having the structure shown in FIG. 1, described above. The parasitic organism can be of a disease associated by the parasite that contains glucokinase or hexokinase, such as American Trypanosomiasis (Chagas' Disease), Human African Trypanosomiasis (African Sleeping Sickness), Leishmaniasis, Malaria, Schistomaisis (Snail Fever), Lyme disease, Filarial diseases, *Helicobacter pylori* infections, the sexually-transmitted disease Gonorrhea (*Neisseria gonorrhoeae*), and other bacterial infections.

IV. Methods of Treatment

Also, a method is provided for treating a mammal that is infected by a parasitic organism (e.g., a bacterial infection). This method comprises administering to the disease-affected mammal a composition comprising a pharmaceutically acceptable carrier and the compound of FIG. 1, described above. Examples of such disease-affected mammals include humans and domestic animals (e.g. dogs, cats, and thereof).

Example 1

Here, the X-ray crystal structures are reported of TcGlcK in its complexes with inhibitors 2-benzamido-2-deoxy-D-glucopyranose (benzoyl glucosamine, abbreviated BENZ-GlcN) as shown in FIG. 2b; 2-N-carboxybenzyl-2-deoxy-D-glucosamine (carboxybenzyl glucosamine, abbreviated CBZ-GlcN) as shown in FIG. 2a; 2-[[3-(4-hydroxyphenyl)-1-oxopropyl]amino]-2-deoxy-D-glucosamine (hydroxyphenyloxopropyl glucosamine, abbreviated HPOP-GlcN) as shown in FIG. 2c; and 2-[[1,1-dioxobenzo[b]thiophen-2-yl]methyloxocarbonylamino]-2-deoxy-D-glucosamine (dioxobenzylthiophenyl glucosamine, abbreviated DBT-GlcN) as shown in FIG. 2d. These inhibitors present the molecular details for affinity in the active site and may disclose more inhibitor design possibilities that can be used for optimized selectivity and potency. The inhibitor kinetics are presented of the aforementioned inhibitors with enzymes TcGlcK and HsGlcK. Specifically, the glucosamine analogues BENZ-GlcN, CBZ-GlcN, HPOP-GlcN, and DBT-GlcN were tested against the qualified drug-target *T. cruzi* glucokinase as potentially potent and/or selective inhibitors The synthesis and characterization are shown for HPOP-GlcN and DBT-GlcN, whereas inhibitors BENZ-GlcN and CBZ-GlcN were commercially available. Finally, in-vitro inhibition assays against *T. cruzi* parasites co-cultured in NIH/3T3 fibroblasts are effectively demonstrated for glucosamine analogues BENZ-GlcN and CBZ-GlcN.

Experimental Procedures

Materials.

N-Cbz-D-glucosamine (CBZ-GlcN), 2-benzamido-2-deoxy-D-glucopyranose (BENZ-GlcN), and isopropyl β-D-thiogalactopyranoside (IPTG) were purchased from Carbosynth. Hexadeuterodimethyl sulfoxide ($D_6$-DMSO, 99.96 atom %), tetrahydrofuran (anhydrous grade), 3-(4-hydroxyphenyl)propionic acid N-hydroxysuccinimide ester (≥97.0%), ammonium formate (HPLC grade, ≥99.0%), acetonitrile (HPLC grade), ethylenediaminetetraacetic acid tetrasodium salt hydrate (>99.0%), imidazole (99+%), bovine pancreas deoxyribonuclease I (DNase I), bovine pancreas ribonuclease A (RNase A), D-(+)-glucosamine hydrochloride (≥99%), triethanolamine (≥99.0%), sodium citrate tribasic dihydrate (≥99.0%), carboxymethyl (CM) cellulose, *Saccharomyces cerevisiae* glucose-6-phosphate dehydrogenase (type XV), β-nicotinamide adenine dinucleotide phosphate hydrate (NADP⁺, ≥95%), adenosine 5'-triphosphate disodium salt hydrate (ATP, 99%), D-glucose-6-phosphate sodium salt (≥98%), and all buffer salts (≥98%) were purchased from Sigma. Cobalt-nitrilotriacetic acid (Co-NTA) resin, methanol, ethyl acetate, lysozyme (type VI), triethylamine, DL-dithiothreitol (DTT), 2×YT broth, Luria-Bertani (LB) broth, kanamycin sulfate, protease inhibitor tablets (EDTA-free), 1,1-dioxobenzo[b]thiophen-2-ylmethyl N-succimidyl carbonate (95%), and all other chemicals were purchased from Fisher Scientific.

Cloning.

The following genes: *Trypanosoma cruzi* glucokinase, strain CL Brener (GenBank accession number XP_821474) and *Homo sapiens* glucokinase (hexokinase IV) (UniProtKB accession code P35557) were cloned into separate kanamycin-resistant pET-28a(+) *Escherichia coli* expression vectors at restriction sites 5' NcoI and 3' HindIII at Genewiz, Inc. (South Plainfield, N.J.). Codons in all plasmids were optimized for protein expression. These plasmid constructs were designated as pET-TcGlcK and pET-HsGlcK, respectively. Each construct encodes for an N-terminal hexahistidine tag. The pET-TcGlcK plasmid encodes the segment MGRGSHHHHHHGMA that precedes the start methionine and the 9-residue segment VGKKQKAQL at the C-terminal region was not included. The CL Brener strain of *T. cruzi* glucokinase differs at eight positions compared to the previously reported construct used by Cordiero and colleagues in the first X-ray crystal structure determination of TcGlcK; see PDB entry 2Q2R (1). These positions in the CL Brener strain of TcGlcK include the following changes: A22V, I65L, M81I, H125R, L213I, F232L, H327R, and S344T. The pET-HsGlcK plasmid encodes the segment MGHHHHHHENLYFQGM that precedes residue K12 (N-terminal segment M1-A11 of HsGlcK was not included) and the 8-residue segment KKACMLGQ at the C-terminal region was also not included. This HsGlcK gene was based off a construct used in X-ray crystallography experiments (2).

Expression and Purification of TcGlcK and HsGlcK.

Each protein expression of either TcGlcK or HsGlcK followed a similar protocol and was performed separately. Transformation of plasmids pET-TcGlcK and pET-HsGlcK was performed by the heat shock method using *E. coli* strain BL21(DE3) (Agilent Technologies) and colonies were grown on Luria-Bertani (LB) agar plates with 50 µg/mL of kanamycin. Starter cultures containing 5 mL of 2×YT broth, 50 µg/mL of kanamycin, and a single colony of *E. coli* from the transformation step were incubated at 37° C. and shaking at 250 rpm for 8 hr. The starter cultures were used to inoculate six 2 L culture flasks containing 1 L of 2×YT broth and 50 µg/mL of kanamycin that followed a 16 hr incubation at 37° C. and shaking at 220 rpm. The 1 L cultures were induced with IPTG to a final concentration of 1 mM and were incubated for an additional 24 hrs at 28-32° C. with shaking at 220 rpm. The *E. coli* were centrifuged and the cell pellets were stored at −80° C. overnight. Each pellet was thawed to room temperature and resuspended in lysis buffer [25 mM HEPES (pH 7.0), 150 mM NaCl]. Cell lysis was performed by adding lysozyme and the cell suspensions were stirred for 1 hr at 4° C. before adding EDTA-free protease inhibitor tablets, after which the cell lysates were sonicated for 30 minutes in a water-bath sonicator (FS20, Fisher Scientific) and stored at −20° C. overnight. Cell lysates were thawed to room temperature and DNase I and RNase A at final concentrations of 8 µg/mL and 13 µg/mL, respectively, were added and stirred at 4° C. for 1 hr, followed by overnight freezing at −80° C. Cell lysates were thawed to room temperature and centrifuged at 15,000 rpm for 45 min at 4° C. and the resulting supernatants were recovered and loaded onto separate cobalt-nitrilotriacetic acid (Co-NTA) immobilized-metal affinity chromatography (IMAC) columns [1.5 cm (internal diameter)×4.5 cm (bed height)] that were pre-equilibrated with mobile phase A [25 mM HEPES (pH 7.0), 150 mM NaCl]. Mobile phase A was used as an initial wash to aid in eluting protein impurities followed by an isocratic step to 13% mobile phase B, where 100% mobile phase B was 50 mM HEPES (pH 7.0), 300 mM NaCl, 150 mM imidazole. After the UV absorbance ($\lambda$=280 nm) on the chromatograms reached baseline, gradient elutions from 13-100% mobile phase B (50 mL gradient) were used to elute most of the other impurities from the columns.

Fractions of TcGlcK resulting from the Co-NTA step were pooled and concentrated to 5 mL using an Amicon centrifugal concentrator (Millipore) equipped with a YM-30 membrane (30 kDa molecular weight cutoff (MWCO)). The sample was loaded onto a 16/600 size-exclusion column (GE Healthcare) that was pre-equilibrated with 50 mM HEPES (pH 7.5), 0.2 imidazole, 2 mM MgCl₂, which was the required solution for crystallization experiments (see below). Sodium dodecyl sulfate-polyacrylamide gel electrophoresis (SDS-PAGE) revealed the final fractions to be ≥99% pure. For crystallization, TcGlcK fractions were pooled and concentrated to 11.2 mg/mL [$\epsilon_{280}$=33,710 M⁻¹ cm⁻¹ (3); M.W.=42,174 g/mol (monomer of His-tagged TcGlcK)]. For activity assays, TcGlcK was buffer-exchanged into 50 mM triethanolamine (pH 7.6) by using a PD-10 desalting column (GE Healthcare) followed by adjusting the enzyme concentration to 1.0 mg/mL.

Fractions of HsGlcK resulting from the Co-NTA step (see above) were pooled and concentrated to 5 mL using an Amicon centrifugal concentrator (YM-30 MWCO membrane) and loaded onto a 16/600 size-exclusion column that was pre-equilibrated with assay buffer (50 mM triethanolamine (pH 7.6)). Pure fractions, as determined by SDS-PAGE, were pooled and concentrated to 1.0 mg/mL [$\epsilon_{280}$=32,430 M⁻¹ cm⁻¹ (3); M.W.=52,068 g/mol (monomer of His-tagged HsGlcK)].

Crystallization of *T. cruzi* Glucokinase.

Crystals of TcGlcK (in the absence of glucose) were prepared by the sitting-drop vapor diffusion method by combining a 1.0 µL drop of enzyme solution [5.5-7.5 mg/mL TcGlcK, 50 mM N-(2-hydroxyethyl)piperazine-N'-(2-ethanesulfonic acid) (HEPES, pH 7.5), 0.2 M imidazole, 2 mM MgCl₂] and a 1.0 µL drop of precipitant solution [12-24% (w/v) PEG 3,350, 0.1 M sodium citrate (pH 7.0)] on a 96-well sitting-drop plate (Innovadyne) and was equilibrated against 90 µL of precipitant solution at room temperature and stored inside a Styrofoam container to avoid unwanted temperature fluctuations. Single crystals appeared after 1 day but matured after two weeks of growth. Large crystals of the batch were subsequently soaked in solutions containing an inhibitor. A crystal of the TcGlcK-BENZ-GlcN complex was prepared by soaking an unliganded single crystal of TcGlcK (as grown from a precipitant solution having 20% (w/v) PEG 3,350) in a soak solution [1.0 mM BENZ-GlcN, 5.0% (v/v) dimethyl sulfoxide (DMSO), 0.1 M sodium citrate (pH 7.0), 20% (w/v) PEG 3,350] for 28 hr at room temperature. A crystal of the TcGlcK-CBZ-GlcN complex was prepared by soaking a large single crystal of the unliganded TcGlcK form (as grown from a precipitant solution having 12% (w/v) PEG 3,350) in a soak solution [1.0 mM CBZ-GlcN, 5.0% (v/v) DMSO, 0.1 M sodium citrate (pH 7.0), 15% (w/v) PEG 3,350] for 24 hr at room temperature. A crystal of the TcGlcK-HPOP-GlcN complex was prepared by soaking a large single crystal of the unliganded TcGlcK form (as grown from a precipitant solution having 16% (w/v) PEG 3,350) in a soak solution [1.0 mM HPOP-GlcN, 5.0% (v/v) DMSO, 0.1 M sodium citrate (pH 7.0), 18% (w/v) PEG 3,350] for 24 hr at room temperature. A crystal of the TcGlcK-DBT-GlcN complex was prepared by soaking a large single crystal of the unliganded TcGlcK form (as grown from a precipitant solution having 20% (w/v) PEG 3,350) in a soak solution [1.0 mM DBT-GlcN, 5.0% (v/v) DMSO, 0.1 M sodium citrate (pH 7.0), 22% (w/v) PEG 3,350] for 24 hr at room temperature. All crystals were transferred into their corresponding cryoprotectant solutions [soak solution supplemented with 25% (v/v) glycerol] and allowed to be exposed for no longer than ~10-15 sec prior to being flash-cooled in liquid nitrogen.

Activity Assays of TcGlcK and HsGlcK.

Enzymatic activity of glucokinase from *T. cruzi* and *H. sapiens* were both performed using a similar protocol but had minor modifications. In general, a two-enzyme coupled colorimetric assay was performed, as previously described (4). The assay is based on the formation of NADPH ($\lambda_{max} \approx 340$ nm; $\epsilon_{340} = 6,220$ M$^{-1}$ cm$^{-1}$) (5). In the 1$^{st}$ step of the assay, glucokinase/hexokinase in the presence of Mg$^{2+}$, ATP, and D-glucose react to form glucose-6-phosphate (G-6-P) and ADP. In the 2$^{nd}$ step, glucose-6-phosphate dehydrogenase (G6PDH) in the presence of the formed G-6-P and NADP$^+$ react to form 6-phosphogluconolactone and NADPH. All measurements were performed in triplicate at 22° C.

TcGlcK assays used purified enzyme (0.12 µM for the monomer (0.0051 mg/mL)) that was used in the reaction mixtures, which were carried out with *S. cerevisiae* G6PDH (0.0064 mg/mL) in an assay buffer [50 mM triethanolamine (pH 7.6), 7.95 mM MgCl$_2$, 0.55 mM ATP, 0.55 mM NADP$^+$] contained substrate ([D-glucose] ranged from 0.2-15.0 mM) and inhibitor ([BENZ-GlcN] ranged from 0-20 µM; [CBZ-GlcN] ranged from 0-10 µM; [HPOP-GlcN] ranged from 0-10 µM; and [DBT-GlcN] ranged from 0-20 µM). Reactions were performed at room temperature (22° C.) and were terminated after 120 sec (optimal time) using 90 µL of 1.5 M EDTA (pH 8.0). The EDTA solution was prepared from the tetrasodium salt. For quantification of NADPH, UV-visible spectrophotometric absorbance readings were recorded at 338 nm ($\lambda$) with an Agilent 8453 UV-visible spectrophotometer exactly 1 min after solutions were treated with the EDTA solution. Concentration of NADPH was determined through Beer's Law using the molar absorptivity of 6,220 M$^{-1}$ cm$^{-1}$.

HsGlcK assays were performed at room temperature and used the same protocol implemented for TcGlcK (see above) except that the reactions were terminated after 600 sec (optimum time) with 90 µL of 1.5 M EDTA (pH 8.0) and the reaction mixtures had slight modification. Briefly, DTT, which reduces disulfide bonds was added to the stock solution aliquot of HsGlcK on the day of the experiment (e.g. 1.0 µL of 20 mM DTT was mixed with 99.0 µL of 1.0 mg/mL HsGlcK) and was allowed to pre-equilibrate at 4° C. for 30 min prior to running assay reactions. Purified HsGlcK (0.15 µM for the monomer or 0.0077 mg/mL) and *S. cerevisiae* G6PDH (0.0064 mg/mL) in an assay buffer [50 mM triethanolamine (pH 7.6), 7.95 mM MgCl$_2$, 5.0 mM ATP, 0.55 mM NADP$^-$, 1.0% (v/v) DMSO, 1.0 mM DTT, 5.0 mM KCl] contained substrate ([D-glucose] ranged from 5.0-50.0 mM) and inhibitor ([BENZ-GlcN] ranged from 0-500 µM; [CBZ-GlcN] ranged from 0-500 µM; and [HPOP-GlcN] ranged from 0-500 µM). DBT-GlcN was not used in the inhibition enzymatic assays because this compound absorbs light at the wavelength of NADPH (338 nm) at the concentrations needed for any reasonable inhibition of HsGlcK.

X-Ray Crystal Structure Determinations.

X-ray diffraction data from single crystals of the TcGlcK-CBZ-GlcN complex, the TcGlcK-HPOP-GlcN complex, and the TcGlcK-DBT-GlcN complex were collected on NE-CAT beamline 24ID-E ($\lambda = 0.9792$ Å). Data from a single crystal of the TcGlcK-BENZ-GlcN complex was collected on NE-CAT beamline HF-4M ($\lambda = 0.9791$ Å). The HKL-2000 suite allowed for the processing of the diffraction data through indexing, integration, and scaling (6); however, for the TcGlcK-BENZ-GlcN complex, diffraction data was processed using the following programs: XDS (7), AIMLESS (8), and POINTLESS (9). Data for the structures were processed using the P2$_1$ space group and these crystals had similar unit cell dimensions. The program Phaser (10) as part of the CCP4 suite (11) was used to produce a molecular replacement result for each structure. The search model used was the A-chain structure of TcGlcK (PDB entry 2Q2R) (1) less ligand atoms and solvent atoms.

Refinement was performed with Phenix (version 1.8.2_1309) (12-15). Model building was performed using Coot (version 0.6.2) (16). Water molecules were included in the later stages of refinement. In all crystal structures having ligand complexes reported herein, inhibitors in the A- and B-chains were refined with full occupancy. Additionally, average B-factors for ligands BENZ-GlcN, CBZ-GlcN, HPOP-GlcN, and DBT-GlcN of their corresponding crystal structures were similar to their whole protein main chain average B-factors (Table 1). From the molecular replacement model (PDB entry 2Q2R), 8 residue positions were mutated to the corresponding residues for the CL Brener strain of TcGlcK using Coot and residues preceding the start methionine in all structures were not included. Disordered residues found at a loop segment (residues G43-N45) for the TcGlcK-HPOP-GlcN complex and the TcGlcK-DBT-GlcN complex were excluded from the final models. Data collection and refinement statistics for all structure determinations are provided in Table 1:

TABLE 1

Data Collection and Refinement Statistics.

| | Tc GlcK-BENZ-GlcN | Tc GlcK-CBZ-GlcN | Tc GlcK-HPOP-GlcN | Tc GlcK-DBT-GlcN |
|---|---|---|---|---|
| Data Collection | | | | |
| resolution limits (Å) | 50.0-2.40 | 50.0-2.50 | 50.0-2.10 | 50.0-1.90 |
| total/unique reflections measured | 136171/31494 | 105321/28549 | 160176/46434 | 251662/62066 |
| space group symmetry unit cell dimensions | P2$_1$ | P2$_1$ | P2$_1$ | P2$_1$ |
| a, b, c (Å) | 68.6, 78.8, 76.6 | 68.7, 79.0, 76.4 | 68.1, 80.0, 75.8 | 68.2, 78.7, 75.4 |
| α, β, γ (deg) | 90.0, 94.5, 90.0 | 90.0, 94.7, 90.0 | 90.0, 95.0, 90.0 | 90.0, 94.8, 90.0 |

TABLE 1-continued

Data Collection and Refinement Statistics.

|  | Tc GlcK-BENZ-GlcN | Tc GlcK-CBZ-GlcN | Tc GlcK-HPOP-GlcN | Tc GlcK-DBT-GlcN |
|---|---|---|---|---|
| $R_{merge}{}^{a,b}$ | 0.079 (0.822) | 0.101 (0.694) | 0.067 (0.389) | 0.040 (0.440) |
| $I/\sigma(I)^a$ | 12.9 (1.4) | 13.26 (2.17) | 18.96 (2.86) | 26.73 (3.00) |
| completeness (%)$^a$ | 98.5 (92.0) | 99.8 (100) | 98.5 (97.4) | 99.1 (98.6) |
| Refinement |  |  |  |  |
| reflections used in refinement/test set | 59783/3023 | 28332/1434 | 46407/2342 | 62037/3148 |
| $R_{work}{}^c$ | 0.1929 | 0.1902 | 0.1905 | 0.1972 |
| $R_{free}{}^d$ | 0.2564 | 0.2304 | 0.2368 | 0.2373 |
| protein chains$^e$ | 2 | 2 | 2 | 2 |
| protein residues$^e$ | 734 | 734 | 728 | 731 |
| protein atoms$^e$ | 5696 | 5696 | 5654 | 5675 |
| solvent molecules$^e$ | 87 | 4 | 244 | 201 |
| ligand molecules$^e$ | 2 | 2 | 2 | 2 |
| metal ions$^e$ | 0 | 0 | 0 | 0 |
| Root Mean Square Deviation$^f$ |  |  |  |  |
| bonds (Å) | 0.009 | 0.010 | 0.009 | 0.009 |
| angles (deg) | 1.30 | 1.20 | 1.20 | 1.20 |
| Average B-factors$^g$ (Å$^2$) |  |  |  |  |
| main chain | 43 | 79 | 42 | 53 |
| solvent | 32 | 60 | 40 | 48 |
| ligand | 31 | 73 | 38 | 48 |
| Ramachandran Plot$^f$ (%) |  |  |  |  |
| allowed | 89.7 | 89.1 | 91.4 | 90.5 |
| additionally allowed | 10.0 | 10.8 | 8.5 | 9.4 |
| generously allowed | 0.3 | 0.2 | 0.2 | 0.2 |
| disallowed | 0.0 | 0.0 | 0.0 | 0.0 |
| PDB accession code | 5BRD | 5BRE | 5BRF | 5BRH |

$^a$Values in parenthesis are for the highest resolution shell.
$^bR_{merge} = \Sigma|I - <I>|/\Sigma I$, where I is the observed intensity, <I> is the average intensity calculated from replicate data.
$^cR = \Sigma|F_o| - |F_c|/\Sigma|F_o|$ for reflections contained in the working set.
$^dR_{free} = \Sigma|F_o| - |F_c|/\Sigma|F_o|$ for 10% of reflections contained in the test set held aside during refinement. $|F_o|$ and $|F_c|$ are the observed and calculated structure factor amplitudes, respectively.
$^e$Per asymmetric unit cell.
$^f$Calculated using PROCHECK (17).
$^g$Calculated using MOLEMAN2 (18).

General Procedures for the Synthesis of Glucosamine Analogues.

Reactions were monitored by TLC (silica gel with fluorescent indicator (F-254), 60 Å, 200 μm) using a mobile phase consisting of ethyl acetate/methanol (5:1) and were visualized under UV light. HRMS was performed on a Thermo Fisher Scientific LC-Orbitrap mass spectrometer (model Exactive Plus MS) using heated electrospray ionization (HESI) in positive ion mode. The LC system included a hydrophilic interaction chromatography (HILIC) column containing carbamoyl-silica particles [TSKgel Amide-80, 5 μm, 80 Å, 250 mm×2.0 mm I.D. (TOSOH Bioscience, King of Prussia, Pa.)]. The TSKgel Amide-80 column was selected based on its ability to separate similar monosaccharides (19) so that the final product in each reaction can be separated from unreacted glucosamine. The column was run at a flow-rate of 0.200 mL/min at 25° C. with mobile phase A [50 mM ammonium formate (pH 6.5)] and mobile phase B [100% acetonitrile] that were used for the programmed elution. Mobile phase compositions during elution used the following 5-step program [$1^{st}$-step (95% MP-B for 10 min); $2^{nd}$-step (95-85% MP-B in 5 min); $3^{rd}$-step (85% MP-B for 15 min); $4^{th}$-step (85-75% MP-B in 5 min); $5^{th}$-step (75% MP-B for 15 min)]. 1-Dimensional and 2-Dimensional $^1$H and $^{13}$C NMR spectra were recorded on a Bruker Avance 700 spectrometer equipped with a cryoprobe operating at 700.07 MHz for $^1$H nuclei and 125.5 MHz for $^{13}$C nuclei equipped with a room temperature inverse detection probe. Topspin software (version 3.1, Bruker) was used for data processing. $^1$H NMR and $^{13}$C NMR chemical shifts (δ) are reported in ppm relative to the TMS signal and $^1$H—$^1$H average coupling constants (J) are reported in Hz.

Synthesis of 2-[[3-(4-hydroxyphenyl)-1-oxopropyl]amino]-2-deoxy-D-glucosamine (HPOP-GlcN)

Hydrolysis of D-(+)-glucosamine hydrochloride (362 mg, 1680 μmol) with 3-(4-hydroxyphenyl)propionic acid N-hydroxysuccinimide ester (221 mg, 840 μmol) in a solution of THF (26.7 mL), deionized water (13.3 mL), and triethylamine (1.0 mL) was performed at room temperature by allowing the solution to stir vigorously for 1.5 hr. The reaction mixture was concentrated down (rotovap) to ~10 mL and 10 mL of acetonitrile was added to help make the solution homogeneous. This resulting solution was syringe filtered (0.22 μm) and used as the sample for semi-preparative HPLC using a HILIC column [TSKgel Amide-80, 10 μm, 80 Å, 300 mm×7.8 mm I.D.] and monitoring absorbance using a UV detector ($\lambda_{max}$ of HPOP-GlcN=278 nm). Although the $\lambda_{max}$ for the sample is at 278 nm, in order to upscale the sample injection volume but avoiding a saturated UV response, the wavelength was set to 292 nm and was used for sample injections of 100 μL. The following HPLC conditions were used: flow-rate=3.0 mL/min, UV-detector (λ=292 nm), sample volume=100 μL, room temperature, MP-A [50 mM ammonium formate (pH 6.5)], and MP-B [100% acetonitrile]. Mobile phase compositions during elution used the following 5-step program [1$^{st}$-step (95% MP-B for 10 min); 2$^{nd}$-step (95-90% MP-B in 10 min); 3$^{rd}$-step (90% MP-B for 20 min); 4$^{th}$-step (90-50% MP-B in 5 min); 5$^{th}$-step (50% MP-B for 5 min)]. Eight sample injections were run, and all fractions were pooled (~100 mL) and concentrated down (rotovap) to ~1 mL and complete solvent removal was achieved by speed-vacuum overnight to afford compound HPOP-GlcN as an off-white powder (10.2 mg, 92.7%).

Synthesis of 2-[[1,1-dioxobenzo[b]thiophen-2-yl] methyloxocarbonylamino]-2-deoxy-D-glucosamine (DBT-GlcN)

Hydrolysis of D-(+)-glucosamine hydrochloride (362 mg, 1680 μmol) with 1,1-dioxobenzo[b]thiophen-2-ylmethyl N-succimidyl carbonate (283 mg, 840 μmol) in a solution of THF (20 mL), deionized water (20 mL), and triethylamine (1.0 mL) was performed at room temperature by allowing the solution to stir vigorously for 1.5 hr. The reaction mixture was concentrated down (rotovap) to ~15 mL and 5 mL of acetonitrile was added to make the mixture homogenous. This resulting solution having an orange/yellow color was used as the sample for semi-preparative HPLC and was performed under the same conditions as for HPOP-GlcN, except that the sample volumes were 100 μL and the wavelength on the UV detector was set to λ=310 nm to avoid signal saturation (note: $\lambda_{max}$ of DBT-GlcN=269 nm). Ten separate sample injections were run and all fractions were pooled (~130 mL) and concentrated down (rotovap) until all of the solvent was removed. An oil residue was barely observed on the round-bottom flask and 1.0 mL of 90% (v/v) acetonitrile was used to dissolve the compound. The sample was concentrated by speed-vacuum overnight and afforded compound DBT-GlcN as a red/orange oil (13.8 mg, 82.1%).

Results and Discussion

Based on the structural features important for substrate recognition in the active site of TcGlcK, we designed and synthesized potential TcGlcK inhibitors based on the glucose-like scaffold. As shown in FIGS. 2a-2d, the compounds all share a common glucosamine moiety to preserve key enzyme-substrate hydrogen bond interactions with the monosaccharide C1, C2, C3, C4, and C6 hydroxyl groups. However, each compound differs in the nature of its tail group designated to interact with the outer active site.

Table 2 shows inhibition constants ($K_i$) for the glucosamine analogues in FIGS. 2a-2d when tested against TcGlcK and HsGlcK. HsGlcK is also referred to as *Homo sapiens* hexokinase IV (HsHxK IV) and was chosen as the hexokinase isoenzyme for inhibition assays. The observed trend is that these inhibitor compounds have much lower $K_i$ values with TcGlcK (stronger inhibition) when compared to HsGlcK (weaker inhibition), indicating that the compounds are more selective towards the *T. cruzi* glucokinase. A selectivity ratio is also shown in the far right column of Table 2 for each inhibitor and is defined as the $K_i$ of HsGlcK divided by the $K_i$ of TcGlcK. Higher values of the selectivity ratio indicate better inhibitor selectivity toward TcGlcK.

TABLE 2

Glucokinase Inhibitors.[a,b]

| Inhibitor | $K_i$ versus substrate (μM) | | Glucokinase selectivity ratio[c] |
|---|---|---|---|
| | TcGlcK | HsGlcK | |
| BENZ-GlcN | 32 ± 26 | 376 ± 196 | 12 |
| CBZ-GlcN | 0.71 ± 0.05 | 174 ± 50 | 245 |
| HPOP-GlcN | 1.3 ± 0.6 | 242 ± 97 | 186 |
| DBT-GlcN | 4.1 ± 0.3 | nd[d] | nd[d] |

[a]All compounds were tested as their racemic mixtures (n ≥ 2).
[b]Colorimetric assay, measurements in triplicate.
[c]Selectivity ratio = $K_i$ (HsGlcK)/$K_i$ (TcGlcK).
[d]Not determined.

Example 2

The compounds of FIGS. 2a and 2b were purchased commercially, whereas the compounds of FIGS. 2c and 2d were synthesized and characterized (see above). Of these four compounds, four samples were prepared:

Sample 1: 50 mM of CBZ-GlcN (the compound of FIG. 2a) in 100% DMSO;

Sample 2: 50 mM of BENZ-GlcN (the compound of FIG. 2b) in 100% DMSO;

Sample 3: 50 mM of HPOP-GlcN (the compound of FIG. 2c) in 100% DMSO; and

Sample 4: 50 mM of DBT-GlcN (the compound of FIG. 2d) in 100% DMSO.

Figure 3:
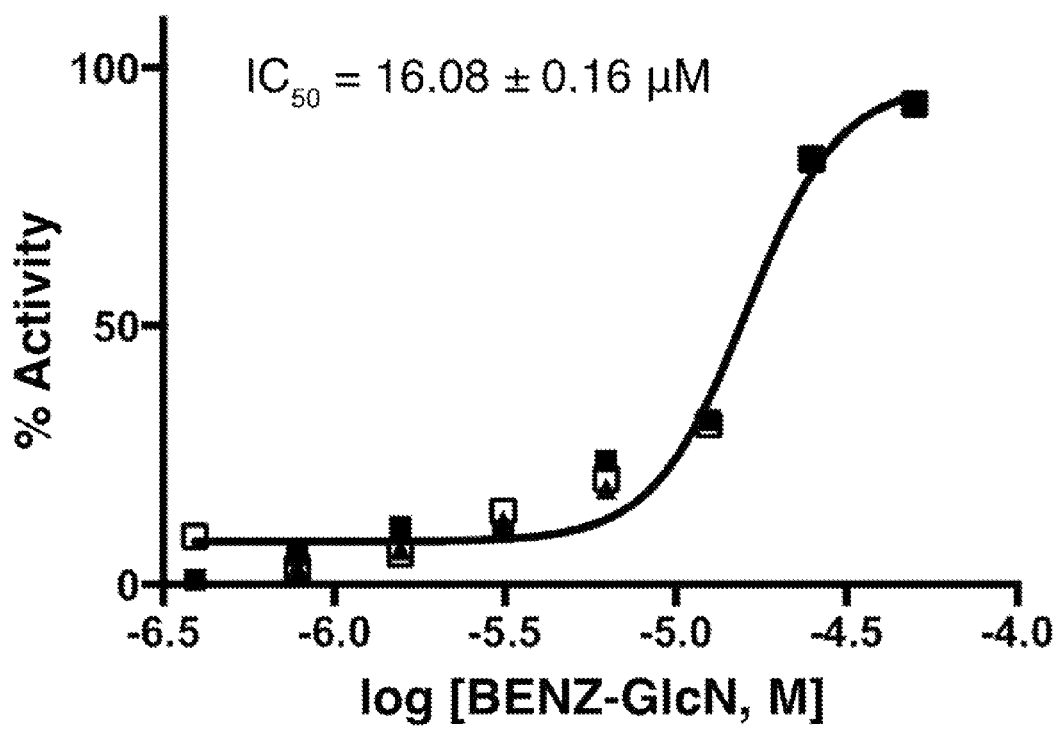
FIG. 3 shows the dose response results for the most potent inhibitor according to the Examples: BENZ-GlcN.

*T. cruzi* (Tulahuen strain) intracellular amastigote parasite cells co-cultured within NIH/3T3 mammalian fibroblast cells were tested for in-vitro growth inhibition from each of Samples 1-4. Dose response results for the most potent inhibitor, BENZ-GlcN (Sample 2), are shown in FIG. 3 that reveals the IC$_{50}$ of 16.08±0.16 μM (the curve and the IC$_{50}$ were calculated from measurements determined in triplicate). Samples 1, 3, and 4 had IC$_{50}$ values>40 μM. The methods used for producing cultures of *T. cruzi* cells and mammalian cells in addition to the methods of performing *T. cruzi* in-vitro inhibition assays were previously described by Andriani and colleagues (20). All biological experimentation was carried out at the Anti-Infectives Screening Core Service Center at New York University School of Medicine, Department of Microbiology.

These and other modifications and variations to the present invention may be practiced by those of ordinary skill in the art, without departing from the spirit and scope of the present invention, which is more particularly set forth in the appended claims. In addition, it should be understood that the aspects of the various embodiments may be interchanged both in whole or in part. Furthermore, those of ordinary skill in the art will appreciate that the foregoing description is by way of example only, and is not intended to limit the invention so further described in the appended claims.

What is claimed:

1. A method of treating a mammal that is infected by a parasitic organism, the method comprising:

administering to the mammal a pharmaceutical compound having the structure

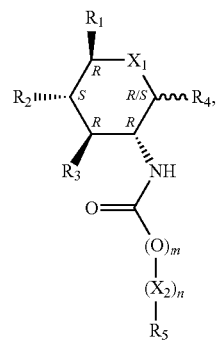

where:

R$_1$, R$_2$, R$_3$, and R$_4$ comprises, independently, H, OH, NH$_2$, SH, or an organic group;

X$_1$ is O, NH, CH$_2$, or S;

m is 1;

X$_2$ comprises an organic linkage;

n is an integer from 0 to 10; and

R$_5$ comprises an aromatic organic group.

2. The method as in claim 1, wherein R$_1$ is a hydroxymethyl group.

3. The method as in claim 1, wherein R$_2$, R$_3$, and R$_4$ are each a hydroxyl group.

4. The method as in claim 1, wherein X$_1$ is O.

5. The method as in claim 1, wherein X$_2$ is CH$_2$.

6. The method as in claim 1, wherein n is 0.

7. The method as claim 1, wherein R$_5$ comprises a benzene group.

8. The method as in claim 1, wherein R$_5$ comprises a phenol group.

9. The method as in claim 1, wherein R$_5$ comprises a benzothiophene group.

10. The method as in claim 9, wherein R$_5$ is a benzothiophene group with a sulfonyl group.

11. The method as in claim 1, wherein the pharmaceutical compound has the structure

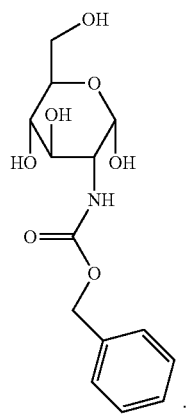

12. The method as in claim 1, wherein the pharmaceutical compound has the structure

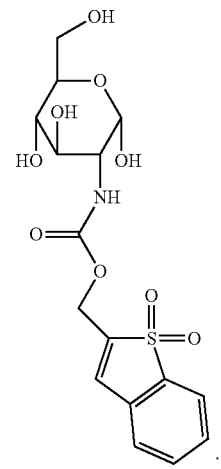

13. A method of treating a mammal that is infected by a parasitic organism, the method comprising administering to the mammal a pharmaceutical compound having the structure

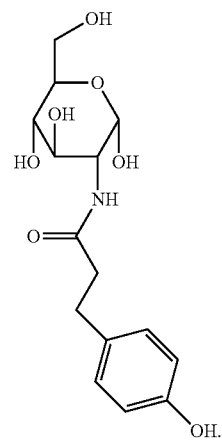

14. A compound having the structure

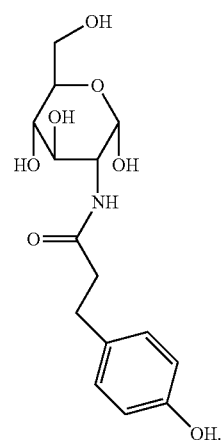

15. A compound having the structure
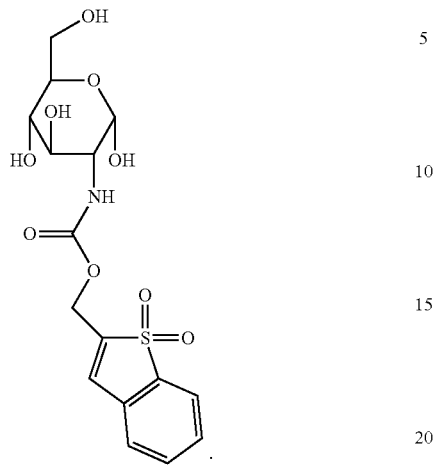
* * * * *